US012324687B1

(12) United States Patent
McNair

(10) Patent No.: US 12,324,687 B1
(45) Date of Patent: *Jun. 10, 2025

(54) PREDICTING CHRONIC KIDNEY DISEASE PROGRESSION

(71) Applicant: CERNER INNOVATION, INC., North Kansas City, MO (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 182 days.

This patent is subject to a terminal disclaimer.

(21) Appl. No.: 18/068,223

(22) Filed: Dec. 19, 2022

Related U.S. Application Data

(63) Continuation of application No. 16/731,595, filed on Dec. 31, 2019, now Pat. No. 11,627,917, which is a
(Continued)

(51) Int. Cl.
*A61B 5/00* (2006.01)
*A61B 5/145* (2006.01)
*A61B 5/20* (2006.01)

(52) U.S. Cl.
CPC ........ *A61B 5/7275* (2013.01); *A61B 5/14546* (2013.01); *A61B 5/201* (2013.01);
(Continued)

(58) Field of Classification Search
CPC ... A61B 5/7275; A61B 5/14546; A61B 5/201; A61B 5/4836; A61B 5/4842; A61B 5/4884; A61B 5/7203; A61B 5/7264
See application file for complete search history.

(56) References Cited

U.S. PATENT DOCUMENTS

2013/0116999 A1* 5/2013 Stein .................... G16H 50/50
703/11
2013/0276513 A1* 10/2013 Sharma .............. G01N 30/7206
73/23.35

(Continued)

OTHER PUBLICATIONS

A. Wang, N. An, Y. Xia, L. Li and G. Chen, "A Logistic Regression and Artificial Neural Network-Based Approach for Chronic Disease Prediction: A Case Study of Hypertension," 2014 IEEE International Conference on Internet of Things (iThings), and IEEE Green Computing and Communications (GreenCom) and (Year: 2014).*

*Primary Examiner* — Sheetal R Paulson
(74) *Attorney, Agent, or Firm* — Kilpatrick Townsend & Stockton LLP

(57) ABSTRACT

Systems, methods, and computer-readable media are provided for identification of patients having an elevated near-term risk of chronic kidney disease progression, including quantitatively predicting whether or not an elevated risk of progression of Stage 3 or Stage 4 chronic kidney disease is likely within a time interval of up to 36 months subsequent to computing the prediction. Based on the prediction, appropriate care providers may be notified so that the risk of CKD progression may be mitigated. In some embodiments, serial measurements are obtained of urine osmolality, and a challenge with an AVP V2 antagonist and serum sodium concentration is provided. From a time series based on the serial measurements, estimates of each variable's velocity and/or doubling-time may be determined. These values then may be combined via a multivariable mathematical model for providing a leading indicator of near-term future abnormalities in kidney function.

20 Claims, 8 Drawing Sheets

Related U.S. Application Data continuation of application No. 15/276,537, filed on Sep. 26, 2016, now Pat. No. 10,531,837.

(60) Provisional application No. 62/232,964, filed on Sep. 25, 2015.

(52) U.S. Cl.
CPC .......... *A61B 5/4836* (2013.01); *A61B 5/4842* (2013.01); *A61B 5/4884* (2013.01); *A61B 5/7203* (2013.01); *A61B 5/7264* (2013.01)

(56) References Cited

U.S. PATENT DOCUMENTS

| | | | | |
|---|---|---|---|---|
| 2014/0079769 A1* | 3/2014 | Terzi | .................... | A61K 9/0019 435/6.12 |
| 2015/0299131 A1* | 10/2015 | Bell | ....................... | A61K 47/36 424/738 |

* cited by examiner

| CKD | eGFR (mL/min/m²) |
|---|---|
| Stage 1 | ≥ 90 |
| Stage 2 | 60 - 89 |
| Stage 3A | 45 - 59 |
| Stage 3B | 30 - 44 |
| Stage 4 | 15 - 29 |
| Stage 5 | < 15 |

Stages 2–3A: Mild symptoms
Stages 3B–4: ↑ Symptoms, ↑ Spend
Stage 5: End-stage / dialysis / KTx

FIG. 3.

```
################################################################

# CERDSM - CKD predictive model - serum sodium, urine osmolality logistic model

########################################################## init value-time array baseline serum sodium, baseline uOsm, and uOsm 4 to 6 hr post-challenge
bct <- matrix(rep(NA,6), nrow=3)

# init intermediate variables
bcn  <- 0
bcu1 <- 0
bcu2 <- 0 init logistic regression coefficients
b <- c(-2.540,0.944,1.303,2.724)

# init output variables
# baseline score = 0 and prob = 7%
CKD.score <- 0
CKD.prob  <- 7 wait until we have 2nd urine specimen separated by 4 to 6 hours from baseline pre-tolvaptan
challenge specimen load specimen-drawn times (in hours delta with respect to tolvaptan administration date-time
stamp)
# baseline serum sodium specimen drawn time may be up to 4 hours prior to baseline urine
specimen
bct[1,2] <- -0.3
bct[2,2] <- -0.1
bct[3,2] <-  4.5 load example lab test results
bct[,1] <- cbind(c(131,355,210)) # Na in mEq/L, uOsm in mOsm/L transform result values
if (bct[1,1] > 135) bcn <- 0 else bcn <- log(135 - bct[1,1] + 1)/3 if (bct[2,1] < 310) bcu1 <- 0 else bcu1 <- log(bct[2,1] - 310 + 1)/7 i <- 0
while (i < 1){
  if (bct[3,1] > bct[2,1]) break
  bcu2 <- max(0,2*(bct[2,1] - bct[3,1])/bct[2,1])
  bcu2 <- 2*exp(-0.00002 + 1.59697*bcu2 + 0.000017*bcu2*bcu2 + 0.071008*bcu2*bcu2*bcu2)/(1 +
exp(-0.00002 + 1.59697*bcu2 + 0.000017*bcu2*bcu2 + 0.071008*bcu2*bcu2*bcu2)) - 1
  i <- i + 1
} update output variables via logistic regression model for likelihood of vaptan efficacy in
retarding CKD progression
CKD.prob <- 100*round(exp(b[1] + b[2]*bcn + b[3]*bcu1 +b[4]*bcu2)/(1 + exp(b[1] + b[2]*bcn +
b[3]*bcu1 +b[4]*bcu2)),2)
CKD.score <- floor((CKD.prob - 7)/8) # 10-level ordinal integer 0 to 9 inclusive.
```

*FIG. 5.*

PREDICTING CHRONIC KIDNEY DISEASE PROGRESSION

CROSS-REFERENCE TO RELATED APPLICATIONS

This application is a continuation of U.S. Non-Provisional application Ser. No. 16/731,595, filed Dec. 31, 2019 which is a continuation of U.S. application Ser. No. 15/276,537, filed Sep. 26, 2016, now U.S. Pat. No. 10,531,837, which claims the benefit of U.S. Provisional Patent Application No. 62/232,964, filed Sep. 25, 2015, each of which is herein incorporated by reference in its entirety.

BACKGROUND

Chronic kidney disease (hereinafter referred to as "CKD") is increasing in epidemiologic and economic importance. In 2010, CKD resulted in 735,000 deaths, a substantial increase compared to 400,000 deaths recorded in 1990. In the U.S., the Centers for Disease Control and Prevention found that between 1999 and 2004, CKD affected an estimated 16.8% of adults 20 years of age and older. Presently, 26 million American adults have CKD. In the U.K., the National Health Service has estimated that 8.8% of the population of Great Britain and Northern Ireland have symptomatic CKD. In 2011, total Medicare expenditures for CKD in the United States exceeded $45 billion. Additionally, diagnoses of cardiovascular-related comorbidities (e.g., hypertension, hypercholesterolemia, diabetes, and cardiovascular disease) increase as CKD becomes worse. Annual health spending increases with increasing severity and comorbidities of CKD, and quality of life diminishes. As a result, accurate diagnosis and prediction of CKD are becoming significantly more important for controlling disease outcomes, and the cost of treatment.

SUMMARY

The present disclosure relates generally to systems, methods, and computer-readable media for identifying patients having an elevated near-term risk of CKD progression (e.g., a risk of progressing from Stage 3 CKD to Stage 4 CKD). Embodiments of the present disclosure are further directed to event prediction, risk stratification, and optimization of the assessment, communication, and decision-making related to CKD in order to prevent, treat, and/or manage CKD in humans. In one embodiment, a platform for embedded decision support in an electronic health record (hereinafter referred to as "EHR") system is provided. Further embodiments of the present disclosure facilitate monitoring human patients to provide quantitative prediction of a degree of risk of CKD progression within a selected time interval. For example, a risk of progression from Stage 3 CKD to Stage 4 CKD in a human patient up to 36 months subsequent to computing the prediction may be provided. Additionally, upon determining a degree of risk of progression of CKD, additional actions, such as informing a care provider clinicians' decisions and renoprotective interventions, may be performed to reduce the risk of progression of CKD and concomitant morbidity in patients.

Thus, an aim of embodiments of the present disclosure relates to automatically identifying persons who are at risk for CKD progression. A further aim of some embodiments of the present disclosure is to reliably distinguish between patients with Stage 3-5 CKD at first classification whose disease (a) remained stable, (b) progressed, or (c) improved in a quantifiable manner to enable accurate decision-making concerning optimal treatment to reduce or delay progression of CKD in those in whom it is probable within a time horizon of up to 36 months. In some embodiments, persons at risk for CKD progression may be identified through the use of serial laboratory measurements and temporal properties of multivariable time series determined from the measurements. The measurements and predictive algorithms may be used in general acute-care venues and afford a degree of robustness against variations in individual physiology, comorbid diagnoses, and severity of illness. Some embodiments further provide a leading indicator of near-term future abnormalities, proactively notifying clinicians caring for a patient, and providing the care providers with sufficient advance notice to enable effective preventive maneuvers to be undertaken when an elevated risk of CKD progression is detected. Additionally, in some embodiments, an indicator may provide notice of the effectiveness (or lack thereof) of alternative therapeutic regimens, and may assist in further decision-making in the medical management of the patient. As a result, a proactive intervention may be implemented for any identified at-risk persons.

Accordingly, in some embodiments, serial measurements of urine osmolality may be obtained for a patient following a challenge with a test dose of an AVP V2 antagonist, such as tolvaptan and/or serum sodium concentration. The measurements may be combined via a multivariable mathematical model and used to provide a leading indicator of near-term responsiveness to the AVP V2 antagonist regimen. In this way, embodiments of the present disclosure facilitate prediction classification or decision-support alert signals to be provided at logistically convenient times far enough in advance of progression to Stage 5 CKD to allow for effective preventive intervention in a majority of cases. Moreover, some embodiments of the present disclosure use commonly available laboratory tests, which may be performed serially to provide data for predictive processes. Thus, the timely determining of, for example, a 36-month predicted likelihood of CKD progression is performed in such a manner so as not to be unduly dependent on scarce or expensive resources, increasing convenience and applicability across widespread populations.

BRIEF DESCRIPTION OF THE DRAWINGS

Embodiments of the present disclosure are described in detail below with reference to the attached figures, which are intended to be exemplary and non-limiting in nature, wherein:

FIG. 3 depicts different stages of CKD and their corresponding estimated glomerular filtration rates, in accordance with an embodiment of the present disclosure;

FIG. 5 depicts one exemplary embodiment of a computer program routine used for predicting risk and/or progression of CKD in an individual, in accordance with an embodiment of the present disclosure.

DETAILED DESCRIPTION

Figure 1A:
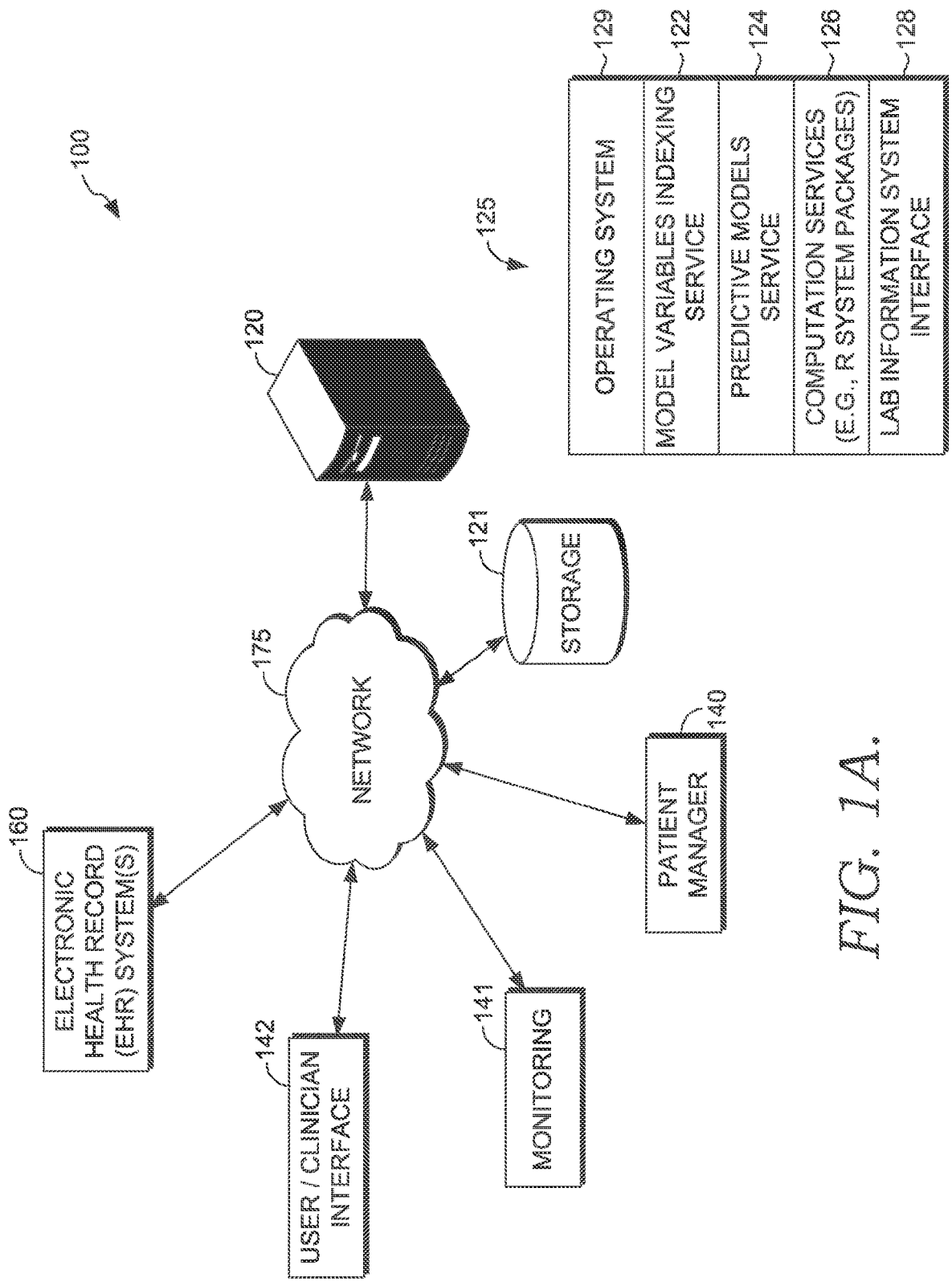
FIGS. 1A-1B depict aspects of an illustrative operating environment suitable for practicing an embodiment of the present disclosure.

The subject matter of the present disclosure is described with specificity herein to meet statutory requirements. However, the description itself is not intended to limit the scope hereof. Rather, the claimed subject matter might also be embodied in other ways, to include different steps or combinations of steps, similar to those described in this document, and in conjunction with other present or future technologies. Moreover, although the terms "step" and/or "block" may be used herein to connote different elements of methods employed, the terms should not be interpreted as implying any particular order among or between various steps or blocks disclosed herein unless and except when the order of individual steps is explicitly described and required.

As one skilled in the art will appreciate, embodiments of the technology may be embodied as, among other things, a method, a system, and/or a set of instructions embodied on one or more computer-readable media. Accordingly, the embodiments may take the form of a hardware embodiment, a software embodiment, and/or an embodiment combining software and hardware. In one embodiment, a computer-program product that includes computer-usable instructions embodied on one or more computer-readable media is provided.

Computer-readable media may include any available media that can be accessed by a computing device, and includes both volatile and non-volatile media, as well as removable and non-removable media. By way of example, and not limitation, computer-readable media may include media implemented in any method or technology for storing information, including computer storage media and communication media. Computer storage media includes both volatile and nonvolatile, as well as removable and non-removable media, implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computing device. Computer storage media does not comprise signals per se. Communication media typically embodies computer-readable instructions, data structures, program modules, or other data in a modulated data signal, such as a carrier wave or other transport mechanism, and includes any information delivery media. The term "modulated data signal" describes a signal that has one or more of its characteristics set or changed in such a manner as to encode information in the signal. By way of example, and not limitation, communication media includes wired media, such as a wired network or direct-wired connection, and wireless media such as acoustic, RF, infrared, or other wireless media. Combinations of any of the above should also be included within the scope of computer-readable media.

In brief, at a high level, this disclosure describes, among other things, methods and systems for identifying persons who are at risk for progression of CKD, or a degree of risk of such a progression. In particular, automatically identifying patients having an elevated near-term risk of CKD progression is provided. Event prediction, risk stratification, and optimization of the assessment, communication, and decision-making to prevent, treat, and/or manage CKD in humans is also provided, and, in one embodiment, takes the form of a platform for embedded decision support in an EHR system. Determining a risk of CKD progression may include analyzing serial laboratory measurements using commonly available laboratory tests, such as urine osmolality, following a challenge with a test dose of an AVP V2 antagonist such as tolvaptan and serum sodium concentration. From these measurements, a multivariable time series may be determined and used for generating a multivariable mathematical model for predicting CKD progression. The measurements and predictive model may be suitable for application in general acute-care venues and afford a degree of robustness against variations in individual physiology, comorbid diagnoses, and severity of illness. Moreover, some embodiments provide a leading indicator of near-term future abnormalities, proactively notifying clinicians caring for a patient, and providing care providers with sufficient advance notice to enable effective preventive maneuvers to be undertaken. Additionally, in some embodiments, the indicator may provide notice of the effectiveness (or lack thereof) of alternative therapeutic regimens, and assist in further decision-making in the medical management of the patient.

Some embodiments of the present disclosure may utilize and/or require as little as two time points (serial laboratory measurements) from a time series to establish a risk of CKD progression in a patient. In addition, if two or more such values are available, then estimates of the probability of responsiveness to an agent or multi drug regimen by the patient may be determined from the time series. De-noised values may be combined using a multi-variable mathematical model. In some embodiments, this may take the form of a logistic regression equation. In other embodiments, the evidence-combining may be implemented via a neural network, a support vector machine, and/or other methods, such as are known to those practiced in the art. In each of these embodiments, a leading indicator of near-term responsiveness to a regimen may be provided. Furthermore, in one exemplary embodiment, a device is integrated with case-management software and/or an electronic health record decision-support system.

By way of example and not limitation, a user using an embodiment of the present technology may provide or withhold AVP V2 antagonist or TNF-alpha inhibitor to a patient with a greater degree of confidence, in addition to alternative interventions. In this exemplary embodiment, the computer system may include an application which, when executed, receives user data from a device, calculates a plurality of time series laboratory test measurements, combines the plurality of time series laboratory test measurements in a mathematical model, and communicates the composite results to a clinician user, case-management software, decision-support system, and/or EHR system, in addition to other possible recipients. For example, the system may notify the user, the user's health plan, EHR decision-support systems, and/or personal health record systems with a message, electronic mail, a call, HTTP, SMS text message, or other form of electronic or radio frequency communication, indicating that the user may be likely to benefit from a disease-modifying medication or treatment regimen. This enables the care providers to take appropriate measures, including determining insurance coverage for the regimen, personnel or medication allocation requirements, or other aspects.

As described in other sections of this disclosure, CKD is increasing in epidemiologic and economic importance in developed nations, and total Medicare expenditures for CKD in 2011 exceeded $45 billion. Further, annual health spending increases with increasing severity and comorbidities of CKD, and quality of life diminishes. Thus, it is advantageous to prevent or delay progression of CKD to the more severe, later stages to the greatest extent possible. This includes reducing or tracking CKD with a high degree of accuracy up to end-stage renal disease (ESRD), at which point renal replacement therapy (dialysis or kidney transplantation) may be needed. The prevalence of Stage 3 to Stage 5 CKD in 2010 was 5.9%. In patients with Stage 3-5 CKD at first classification, the percentage of patients for which the disease (a) remained stable, (b) progressed, or (c) improved in 2010 was approximately 50%, 10-15%, and 25-30% of patients, respectively.

CKD also exhibits significant ethnic variation in its occurrence and progression, mostly due to increased prevalence and severity of hypertension. As an example, 37% of ESRD cases in African Americans can be attributed to high blood pressure, compared with 19% among Caucasians. Treatment efficacy also differs between racial groups. Administration of anti-hypertensive drugs generally halts disease progression in Caucasian populations, but has little effect in slowing renal disease among African American populations, and additional treatments, such as bicarbonate therapy, are often required.

Once patients at risk for CKD progression have been identified, a variety of therapeutic modalities may be used to alter a course of CKD, and/or slow its progression. For example, optimal diabetes therapy (HbA1c target 7%), reduction of proteinuria, aldosterone blockade, and the use of ACEI/ARB antihypertensive therapies may be beneficial, as well as limiting dietary sodium, limiting protein intake, and body weight reduction. Proper treatment for elevated serum phosphorus and parathyroid hormone levels can delay appearance of comorbidities that exacerbate or accelerate progression of CKD. Correction of anemia with erythropoietin therapy is also beneficial in advanced CKD with hemoglobin goals in the 10-12 g/dL range. Additionally, treatment of acidosis may improve CKD progression, and suggests that increasing serum bicarbonate to greater than 20 mmol/L may be beneficial. Approaches to altering the course of CKD by targeting fibroblast growth factor 23 (FGF-23), transforming growth factor β (TGF-β), tumor necrosis factor alpha (TNF-α), neprilysin, and nuclear factor-erythroid-2-related factor 2 (Nrf2) level reductions also may be considered as modalities for reducing and controlling CKD progression.

Use of biomarkers may enable characterizing the biological basis for the heterogeneity of an individual's clinical course and their personalized response to specific treatments, particularly in cancer. The ability to molecularly characterize human diseases presents new opportunities to develop more effective treatments, and also, new challenges for the design and analysis of clinical trials. 'Personalized medicine' is a model for optimizing therapeutics. 'Personalization' posits that the customization of treatment for individual patients can deliver superior clinical outcomes, with improved safety and cost-effectiveness. In such a model, diagnostic tests are essential for selecting the safest and most efficacious treatments, as well as for choosing a dose or administration schedule for the same that best matches the pharmacologic and pathophysiologic particulars of an individual undergoing such treatment. The term 'companion diagnostics' may be used to describe such tests, with molecular assays that measure the levels of specific soluble analytes, proteins, and/or specific gene mutations being used to provide a specific therapy for an individual by stratifying a disease status, selecting a proper medication regimen, and tailoring dosages/administration of selected therapeutics and treatments. Companion diagnostics may be used to aid clinical decision-making to identify patients who are most likely to respond to particular treatments and to identify patients who almost certainly will not benefit from particular treatments. 'Companion diagnostics' (CoDx) may include univariable tests that determine the presence or absence of a receptor that is pertinent to the mechanism of action of the associated therapeutic, or may include univariable tests that determine the level of one particular analyte. Other CoDx's may be 'in vitro diagnostic multivariable index assays' (IVDMIAs). In this connection, multivariable phenotypic profiling may be as important as genotypic profiling in devising personalized medicine treatments.

Further, in some instances, patient therapy may be improved through the identification of targets and surrogate molecular signatures that can help direct appropriate treatment regimens in a patient while taking into account treatment efficacy and drug safety. In particular, patient biofluids or biopsy tissue may be isolated and analyzed for genetic, immunohistochemical, and/or soluble markers to determine if a predictive biomarker signature (e.g., altered concentration of analyte, mutated gene product, differentially expressed protein or pattern of multiple proteins, altered cell surface antigen, etc.) exists as a possible consideration for selecting optimal treatment. These biomarkers may be drug-specific targets and/or differentially expressed nucleic acids, proteins, and/or cell lineage profiles that can directly affect the patient's disease tissue and/or immune response to a therapeutic regimen.

Improvements in diagnostics that can prescreen predictive response biomarker profiles may also be used to optimize patient therapy via molecularly defined, disease-specific treatment. Conversely, patients lacking predictive response biomarkers may no longer needlessly be exposed to drugs that are unlikely to provide clinical benefit, which can enable patients to pursue other therapeutic options and lower overall healthcare costs by avoiding futile treatment. But while patient molecular profiling offers a powerful tool for directing treatment options, the difficulty in identifying disease-specific targets or predictive biomarker signatures that stratify a significant fraction within a disease indication remains challenging.

However, according to an embodiment of the present disclosure, a patient can be predetermined in real time as to whether or not their CKD can be specifically ameliorated by a drug-linked diagnostic vector. Despite growing success in the treatment of CKD achieved with the use of molecular targeted therapy, resistance seems to develop to virtually all of the drugs at some point in time. One way to suppress or delay development of resistance might be through the use of combination therapy. For example, a combined regimen of an AVP V2 antagonist and a TNF-alpha inhibitor may offer synergistic benefits, compared to the same or either therapeutic classes of disease-modifying agents used individually.

Recent trends are moving away from the univariable 'one biomarker: one drug' companion diagnostic scenario, which has characterized the past two decades of targeted drug development, toward a more integrated approach with multiple biomarkers and multi-drug regimens. This 'new paradigm' may pave the way for the introduction of multiplexing strategies using IVDMIAs that utilize multivariable phenotyping as well as gene expression arrays and next-generation sequencing. This holds not only for cancer treatment, but for the treatment of CKD and other chronic diseases as well.

Advances in the understanding of the biology of kidney disease as well as advances in diagnostic technologies, such as the advent of affordable high-resolution DNA sequencing, have had a major impact on the approach to identification of specific alterations in a given patient's condition that could be used as a basis for selecting a CKD treatment, and hence, the development of companion diagnostics. Presently, there are no such 'companion diagnostics' in CKD, even though there are a number of receptor-targeted medications that have annual-cost-of-therapy price tags exceeding $50,000 per year, which is sufficiently high to merit such a companion diagnostic test.

Notably, the action of some disease-modifying therapies (e.g., anti-TNF-alpha agents) may only be evident over a period of many months, while the effect of other disease-modifying therapies may be evidence right away. In that regard, certain biomarkers that characterize an individual's kidney status and responsiveness to one class of agent (e.g., AVP V2 antagonists) may indirectly serve as surrogate measures of responsiveness to other agents whose mechanism of action is different but which nonetheless depend for their effectiveness on a kidney in which CKD has not progressed beyond a certain point.

Accordingly, some embodiments of the present disclosure involve just such a surrogate measure or multivariable predictor. In this connection, the antidiuretic hormone vasopressin may be used for regulating free water clearance in normal physiology. However, vasopressin may have deleterious effects on the kidney. Vasopressin is elevated in animals and patients with CKD. Suppression of vasopressin activity reduces proteinuria, renal hypertrophy, glomerulosclerosis and tubulointerstitial fibrosis in animal models. The potential detrimental influence of vasopressin may be mediated by its effects on mesangial cell proliferation, renin secretion, renal hemodynamics, and blood pressure. Thus, vasopressin response may relate to CKD progression in general and to autosomal dominant polycystic kidney disease in particular. This has led to, over the past several years, the possibility that interventions directed at lowering vasopressin activity, for example by the administration of vasopressin receptor antagonists, may be beneficial in treating CKD.

Tolvaptan, a selective vasopressin V2 receptor antagonist, may also slow the increase in total kidney volume and the decline in kidney function. However, it is as yet unclear (a) which patients are likely to benefit from tolvaptan and which will not, (b) which dose of tolvaptan is optimal, or (c) whether tolvaptan is able to delay progression of CKD to ESRD.

After several decades during which little attention was paid to vasopressin and/or urine concentration in clinical practice, interest in vasopressin has renewed with the availability of new, potent, and orally active vasopressin receptor antagonists—the vaptans—and with the results of epidemiological studies evaluating copeptin (a surrogate marker of vasopressin) in large population-based cohorts. Whether a selective blockade of the different vasopressin receptors may provide therapeutic benefits beyond their present indication in hyponatremia requires new clinical trials at the present time.

Evidence is accumulating that arginine vasopressin (AVP) type 2 (V2) antagonist medications, such as tolvaptan, may normalize hyponatremia and ameliorate progression of CKD in patients who have comorbid heart failure (CHF). Many such patients are refractory to even high-dose loop diuretics and are unable to produce dilute urine. However, AVP antagonist therapy is only effective in a percentage of CKD-CHF patients. Furthermore, AVP antagonist therapy is found to be effective in a considerable percentage of CKD patients who do not have CHF. It is therefore valuable to have diagnostic and prognostic means to identify responders and non-responders to tolvaptan or other AVP antagonist drugs. This is true, in particular, because the current cost of AVP antagonist therapy is high (i.e., greater than $50,000 per year in the U.S. for a single patient) and access to these medications is tightly restricted.

The matter is made further complex by the fact that regulatory-agency-approved on-label clinical indications at the present time state that AVP antagonists are indicated only in the condition of hyponatremia (low concentration of sodium in the blood) and then only in the event that the cause of the hyponatremia is determined to be the syndrome of inappropriate antidiuretic hormone secretion (SIADH). However, observational data accruing from measurements made in patients who received AVP antagonists off-label, even though they were not hyponatremic or only borderline hyponatremic, indicate that AVP antagonists may confer benefits in terms of preserving or restoring kidney function in CKD patients by a mechanism as yet unknown that may be independent of AVP antagonists' effects on sodium metabolism. A further aspect has to do with the frequency with which hyponatremia is caused or exacerbated by antidepressant therapy. In CKD, comorbid clinical depression and prescribing of antidepressants are commonplace.

Patients in earlier stages of CKD (Stages 1-3) bear increased risks for progression to Stage 5 CKD (i.e., ESRD), at which time permanent dialysis therapy or renal transplantation is the only option. Thus, there is a compelling need to predict and prevent CKD efficaciously and, in those for whom prevention is not possible or successful, to undertake effective treatment of CKD as quickly as possible. In some approaches, the principle clinical tools used to detect CKD have been serial measurement of serum creatinine (Cr), blood urea nitrogen (BUN), certain other urine biochemical markers, and measurement of urine output volume per unit of time. However, accurate prediction using such markers is unreliable based on (a) inadequate statistical sensitivity and specificity for the purpose of predicting progression of CKD, and (b) the requirement for prolonged follow-up and repeated measurements over a period of months before guidance is obtained as to a rate of progression of CKD in a particular patient.

The established CKD progression end point of ESRD, or a doubling of serum creatinine concentration (corresponding to a change in estimated glomerular filtration rate [eGFR] of ~57% or greater) is a late event. Bicarbonate concentrations are likewise a lagging indicator. In contrast, embodiments described herein may provide a leading indicator, which may facilitate characterizing prognosis, and also, help to guide therapy, so as to retard the progression of CKD.

Biomarkers such as ADMA and KIM-1 have recently shown promise as leading indicators of CKD progression. However, diagnostics based on measurement of such markers have not yet received regulatory approval and, even when approval is forthcoming, the availability of such tests may likely be limited, particularly in smaller and community-based settings. Thus, another advantage of some embodiments of the present disclosure is to provide diagnostics that utilize biomarkers that are inexpensive and already broadly available.

The role of uric acid (UA) as a biomarker for the progression of CKD remains controversial. Experimental and clinical studies indicate that UA is associated with several risk factors associated with CKD, including diabetes, hypertension, oxidative stress, inflammation, and hyperuricemia. UA could also be considered as a common dominator linking CKD and cardiovascular disease. Notably, the impact of serum UA levels on the survival of CKD, dialysis patients, and renal transplant recipients is also a matter of debate, as there are conflicting results from clinical studies. At present, there is no definite data whether UA is causal, compensatory, coincidental, or if it is only an epiphenomenon in these patients.

Based on the prominence of microvascular changes in the causation of CKD progression, Baumann and colleagues suggest that retinal photography in combination with albuminuria determination may be useful for risk stratification with respect to renal disease progression in patients with CKD Stages 2-4. However, retinal arteriolar narrowing is confounded by aging, hypertension, CKD, and other non-renal vascular processes. Additionally, accurate measurement of retinal arteriolar narrowing by ophthalmologists requires specialized equipment that is not routinely available in ambulatory clinics.

Moreover, some genomics-based or proteomics-based approaches involve cumbersome, complex, expensive, and/or invasive instrumentation. Other recently introduced methods involve measurements, such as genomic or proteomic laboratory tests, that are not widely available, and that have performance turnaround times of many hours or days before the results and predictions are available for use. As a result, a prediction or classification may not be timely with respect to interventions aimed at preventing the predicted progression.

Accordingly, advantages of predictive and diagnostic methods according to embodiments of the present disclosure described herein arise not only in prevention of CKD progression but also in the management of CKD in general. Essentially, some such embodiments constitute a specialized type of so-called 'companion diagnostics' or IVDMIAs that can help to guide optimal selection of therapeutic treatments.

In light of the foregoing, an improved predictive-preventive method and system for management and treatment of CKD has been devised. Embodiments of the methods and systems, including prediction classification and/or decision-support alert signals emitted by the system, are provided at logistically convenient times, and also far enough in advance of progression to Stage 5 CKD to allow for effective preventive intervention in many cases. In some embodiments, the systems and methods include the use of commonly available laboratory tests performed in a serial fashion. For example, the timely determining of a 36-month predicted likelihood of CKD progression may be performed in such a manner so as not to be unduly dependent on scarce or expensive resources, making it more effective, widely applicable, and convenient, which may also result in more efficient treatment protocols with better outcomes.

Referring now to the drawings in general, and initially to FIG. 1A, an exemplary operating environment 100 that is suitable for practicing an embodiment of the present technology is provided. Certain items in block-diagram form are provided for referencing something consistent with the nature of this disclosure, rather than to imply that a certain component is or is not part of a certain device. Similarly, although some items are depicted in the singular form, they may be plural as well (e.g., what is shown as one data store might really be multiple data stores distributed across multiple locations). In this respect, showing every variation of each item might obscure the invention, and thus, for readability, items are provided in the singular, while the plural is also fully contemplated in every instance.

As shown in FIG. 1A, exemplary operating environment 100 provides an aspect of a computerized system for compiling and/or running aspects of the present technology, including collecting and analyzing unstructured text data from electronic health record(s) to assess the texts as to topical or concept-oriented expressions they contain that are statistically similar to those associated with various clinical conditions or diagnoses, to identify which condition/diagnosis-oriented clusters the texts most closely resemble, if any, and to notify the responsible clinicians of those determinations. The system may further suggest consideration of those conditions or diagnoses as part of the constellation of differential diagnoses pertinent to the management of a current patient.

Environment 100 includes one or more EHR systems, such as hospital EHR system 160, which is communicatively coupled to network 175, which is communicatively coupled to computer system 120. In some embodiments, components of environment 100 that are shown as distinct components may be embodied as part of, or within, other components of environment 100. For example, EHR system 160 may comprise one or a plurality of EHR systems, such as hospital EHR systems, health information exchange EHR systems, ambulatory clinic EHR systems, psychiatry/neurology EHR systems, and/or other systems that may be implemented in computer system 120. Similarly, EHR system 160 may perform functions for two or more of the EHR systems (which are not shown).

Network 175 may comprise the Internet, one or more public networks, one or more private networks, and/or any other communications networks, such as a cellular network or other wireless communications network for facilitating communication among devices connected through the network. In some embodiments, network 175 may be determined based on factors such as the source and destination of the information communicated over network 175, the path between the source and the destination, and/or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on data store 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as, for example, wearable, bedside, and/or in-home patient monitors. Although FIG. 1A depicts an exemplary EHR system 160, it is contemplated that an embodiment of the present disclosure may rely on user manager or patient manager 140 and/or monitor 141 for storing and retrieving patient record information, such as information acquired from monitor 141.

Example operating environment 100 further includes user/clinician interface 142 communicatively coupled through network 175 to the EHR system 160. Although environment 100 depicts an indirect communicative coupling between the interface 142 and the EHR system 160 through the network 175, it is contemplated that an embodiment of the interface 142 is directly communicatively coupled to the EHR system 160. An embodiment of the interface 142 takes the form of a user interface operated by a software application or a set of software applications on a client computing device, such as a personal computer, laptop, smartphone, and/or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future events, such as acute risk of deterioration, are determined according to the embodiments presented herein.

Embodiments of the interface 142 also facilitate accessing and receiving information from a user or health care provider about a specific patient or population of patients, including patient history, health care resource data, variables measurements, time series, predictions (including plotting or displaying the determined outcome and/or issuing an alert), or other health-related information. Embodiments of the interface 142 may also facilitate the display of results, recommendations, and/or orders, for example. In an embodiment, interface 142 also facilitates receiving orders for the patient from a clinician/user based on the results of monitoring and predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, and/or other computing devices. In an embodiment, manager 140 includes a Web-based application or a set of applications usable to manage user services provided by an embodiment of the technology. For example, in an embodiment, manager 140 facilitates processing, interpreting, accessing, storing, retrieving, and communicating information acquired from monitor 141, EHR system 160, or storage 121, including candidate diagnoses or conditions determined by embodiments of the technology as described herein. In an embodiment, manager 140 sends a notification (such as an alarm or other indication) directly to user/clinician interface 142 through network 175. In an embodiment, manager 140 sends a maintenance indication to provider clinician interface 142. In one embodiment of the manager 140, an interface component may be used to facilitate access by a user (including a clinician/caregiver or patient) to functions or information on the monitor 141, such as operational settings or parameters, user identification, user data stored on monitor 141, diagnostic services, and/or firmware updates for monitor 141, for example.

As shown in example environment 100, in one embodiment, manager 140 is communicatively coupled to monitor 141 and to network 175. In an embodiment, patient monitor 141 communicates via network 175 to computer system 120 and/or to provider clinician interface 142.

An embodiment of monitor 141 (sometimes referred to herein as a patient-interface component) comprises one or more sensor components operable to acquire clinical or physiological information about a patient, such as various types of physiological measurements, physiological variables, or similar clinical information associated with a particular physical or mental state of the patient, which may be acquired periodically or as one or more time series. In one embodiment, monitor 141 comprises sensors for obtaining and analyzing the serial measurements of urine osmolality and serum sodium concentration. In some embodiments, monitor 141 comprises a patient bedside monitor, such as those used in hospitals to monitor patients. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.), a skin-patch sensor, an ingestible or subdermal sensor, a sensor component integrated into the user's living environment (including the bed, pillow, and/or bathroom), and sensors operable with or through a smartphone carried by a user, for example.

It is also contemplated that the clinical or physiological information about a patient, such as the monitored variables and/or clinical narratives regarding the patient, used according to the embodiment of the present technology disclosed herein, may be received from human measurements, human observations, and/or automatically determined by sensors in proximity to the patient. For example, in one embodiment, a nurse periodically measures a patient's blood pressure and enters the measurement and/or observations via manager 140 or interface 142. In another example, a nurse or caregiver enters one or more progress notes for an in-patient via manager 140 or interface 142. Similarly, values for serial measurements of urine osmolality and serum sodium concentration may be entered via manager 140 or interface 142.

Examples of physiological variables monitored by monitor 141 can include urine osmolality and serum sodium concentration, as described herein. Additionally, in some embodiments, physiological variables monitored by monitor 141 may include, by way of example and not limitation, heart rate, blood pressure, oxygen saturation (SaO2), central venous pressure, other vital signs, and/or any other type of measureable, determinable, and/or observable physiological or clinical variable or characteristic associated with a patient, which in some embodiments may be used for forecasting a future value (e.g., of the measured variable, a composite variable based on one or more of the measured variables, or another factor determined at least in part from one or more of the measured variables, etc.) of a patient in order to facilitate clinical decision-making. In one further embodiment, a monitor, such as monitor 141, may include a sensor probe, such as an Electroencephalogram (EEG) probe, and a communication link that periodically transmits identification information and probe data to patient manager 140, so that the time series of monitored values is stored on patient manager 140, enabling the patient manager 140 to form a raw binary alarm indication and/or a physiological variable decision statistic. In an embodiment, patient monitor 141 collects raw sensor information, such as from an optical sensor, and performs signal processing, such as velocity measurement, forming a physiological variable decision statistic, cumulative summing, trending, wavelet processing, thresholding, computational processing of decision statistics, logical processing of decision statistics, pre-processing or signal condition, and/or any combination of the same, part or all of which may be performed on monitor 141, manager 140, interface 142, and/or computer system 120, or another component not depicted in FIG. 1A.

An embodiment of monitor 141 stores user-derived data locally and/or communicates data over network 175 to be stored remotely. In an embodiment, manager 140 is wirelessly communicatively coupled to monitor 141. Manager 140 may also be embodied as a software application or an application operating on a user's mobile device. In an embodiment, manager 140 and monitor 141 are functional components of the same device, such as a device comprising a sensor and a user interface. In an embodiment, manager 140 is embodied as a base station, which may also include functionality for charging monitor 141 or downloading information from monitor 141. Example operating environment 100 further includes computer system 120, which may take the form of a server, which is communicatively coupled through network 175 to EHR system 160 and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations, such as one or more local clients and/or one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, tablet, cloud-computing device, distributed computing architecture, and/or a portable computing device, such as a laptop, tablet, ultra-mobile P.C., and/or a mobile phone.

Embodiments of computer system 120 include computer software stack 125, which in some embodiments operates in the cloud as a distributed system on a virtualization layer within computer system 120, and includes operating system 129. Operating system 129 may be implemented as a platform in the cloud, and may be capable of hosting a number of services, such as model variables indexing service 122, predictive models service 124, computational services 126 (e.g., R system packages), and lab information system interface 128, for example. Some embodiments of operating system 129 comprise a distributed adaptive agent operating system. Embodiments of services 122, 124, 126, and 128 may run as a local or distributed stack in the cloud, on one or more personal computers or servers such as system 120, and/or on a computing device running patient manager 140 and user/clinician interface 142. In some embodiments, interface 142 operates in conjunction with software stack 125.

In embodiments, model variables indexing service 122 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124, in general, may be responsible for providing multivariable models for predicting CKD, such as those described in connection with method 200 described with respect to FIG. 2.

Computation services 126 perform statistical software operations, and include statistical calculation packages such as, in one embodiment, an R system (the R project for Statistical Computing, which supports R-packages or modules tailored for specific statistical operations, and which is accessible through the Comprehensive R Archive Network (CRAN) at http://cran.r-project.org) or similar services. In an embodiment, computation services 126 include the services or routines which may be embodied as one or more software agents or routines, such as the example embodiments of computer program routines illustratively provided in FIG. 5. In some embodiments, computation services 126 may use EHR or lab information system interface 128, which may provide serial measurements of urine osmolality, serum sodium concentration, and/or other physiological variables. Some embodiments of stack 125 may further use Apache Hadoop and Hbase framework (not shown), or similar frameworks operable for providing a distributed file system, which in some embodiments, facilitate providing access to cloud-based services such as those provided by Cerner Healthe Intent®. Additionally, some embodiments of stack 125 may further comprise one or more stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, and/or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services from various service providers.

Example operating environment 100 also includes storage 121 (or data store 121), which in some embodiments, may include patient data for a candidate or target patient (and/or information for multiple patients), including raw and processed patient data, variables associated with patient recommendations, a recommendation knowledge base, recommendation rules, recommendations, recommendation update statistics, an operational data store which stores events, frequent item sets (e.g., associations such as "X often happens with Y"), and item sets index information, association rule bases, agent libraries, solvers, and solver libraries, and other similar information including data and computer-usable instructions, patient-derived data, and healthcare provider information, for example. It is contemplated that the term data includes any information that can be stored in a computer storage device or system, such as user-derived data, computer-usable instructions, software applications, and/or other information. In some embodiments, data store 121 comprises the data store(s) associated with EHR system 160. Further, although depicted as a single storage data store, data store 121 may comprise one or more data stores, or may be in the cloud.

In some embodiments, computer system 120 is a computing system made up of one or more computing devices. In some embodiments, computer system 120 includes one or more software agents, and in another embodiment, includes an adaptive multi-agent operating system. However, it should be appreciated that computer system 120 may also take the form of an adaptive single agent system or a non-agent system. Computer system 120 may be a distributed computing system, a data processing system, a centralized computing system, a single computer such as a desktop or laptop computer, and/or a networked computing system.

Figure 1B:
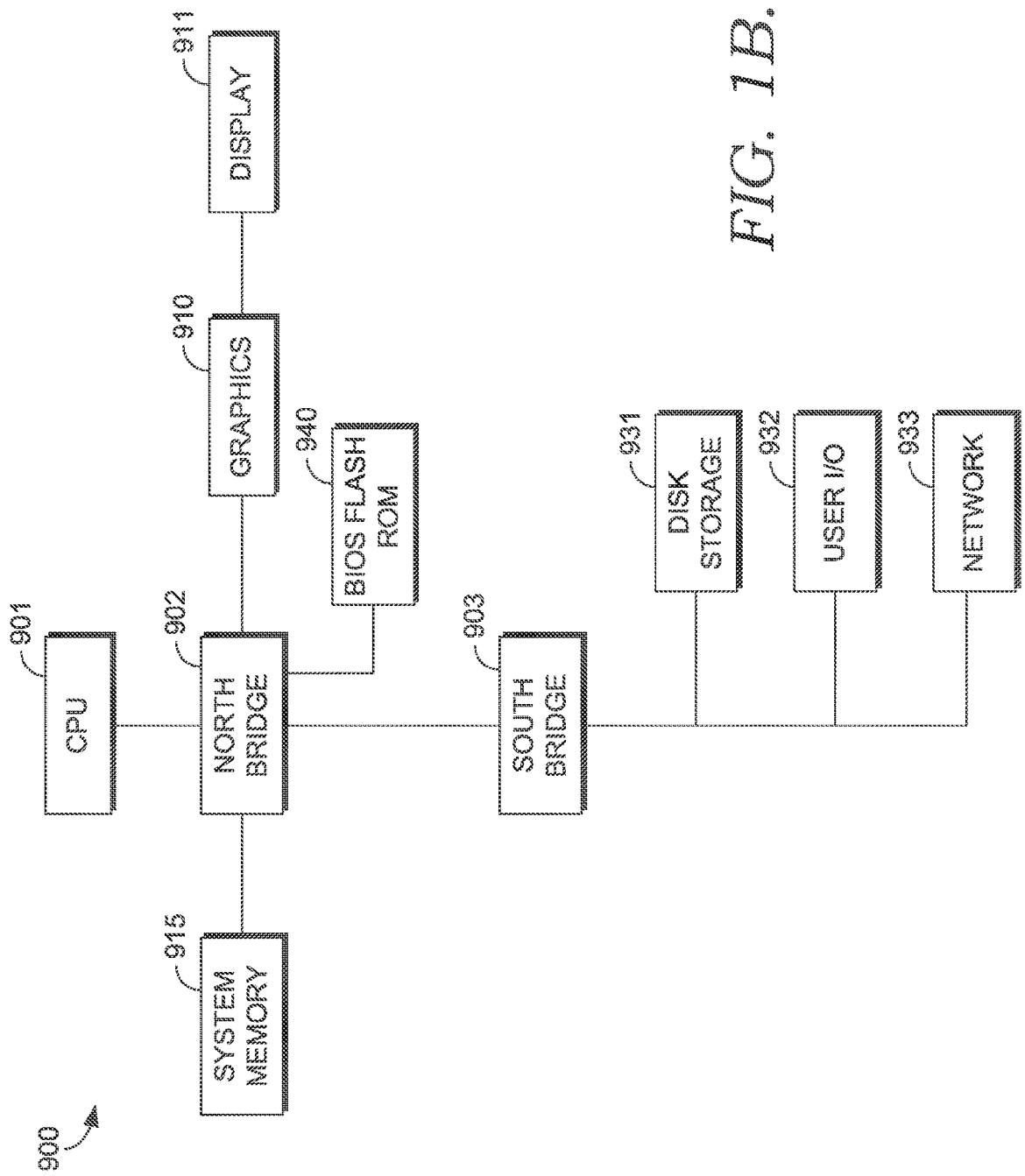

Turning briefly to FIG. 1B, an exemplary embodiment of computing system 900, including software instructions for storage of data and programs in computer-readable media, is provided, in accordance with an embodiment of the present disclosure. Computing system 900 is representative of a system architecture that is suitable for computer systems such as computing system 120. One or more central processing units (CPUs), such as CPU 901, are provided with internal memory for storage of information, and are coupled to north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902, allowing CPU 901 to store instructions and data elements in disk storage 931, which may comprise a fixed disk or USB disk, or to make use of network 933 for remote storage. User I/O device 932, which may comprise a communication device, a mouse, a touchscreen, a joystick, a touch stick, a trackball, and/or keyboard, is coupled to CPU 901 through south bridge 903. The system architecture depicted in FIG. 1B is provided as one example of any number of suitable computer architectures, such as computing architectures that support local, distributed, and/or cloud-based software platforms, and are suitable for supporting computing system 120.

Figure 2:
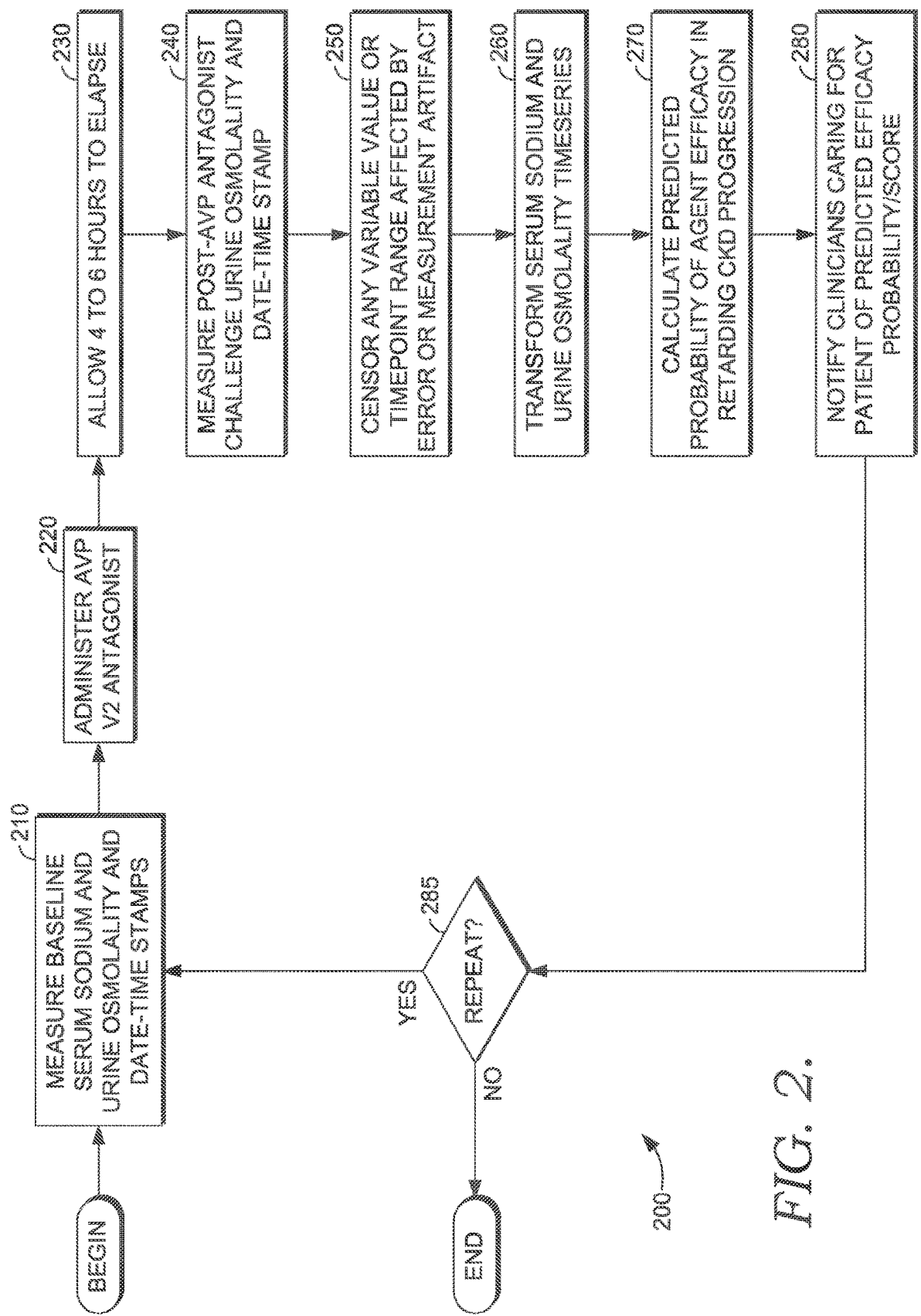
FIG. 2 depicts a block diagram of a method for predicting CKD risk and/or progression in an individual, in accordance with an embodiment of the present disclosure.

Turning now to FIG. 2, a block diagram of an exemplary method 200 for predicting CKD progression is provided, in accordance with an embodiment of the present disclosure. At block 210, recent lab measurements of urine osmolality and serum sodium are received, along with corresponding date-time stamps. These measurements may be received from one or more EHRs, such as EHR 160 or from monitor 141, and may correspond to a subject for which an analysis of CKD progression is performed. At block 220, an AVP V2 antagonist, such as tolvaptan, is administered. At block 230, an amount of time is allowed to elapse to measure the change following the administering of the AVP V2 antagonist. An exemplary elapsed time period may be 4-6 hours (this may also be considered a predetermined or preconfigured time period). The elapsed time may vary based on a particular AVP V2 antagonist that is used. At block 240, a measurement of a new urine osmolality and corresponding date-time stamp is received, following the AVP V2 antagonist challenge. Blocks 210-240 are intended to accumulate the serial measurements of urine osmolality and serum sodium and corresponding data-time stamps for generating a time series of the measurements for each variable. Some embodiments of method 200 accumulate at least a pair of values for each of these variables.

At block 250, any variable value or time point range affected by error or measurement artifact is censored. For example, in some situations, it may be necessary to weed-out measurements that are too close together (e.g., taken at nearly the same time) or too far apart, such that data comparison is not useful or desirable. At block 260, the time series of serum sodium and urine osmolality is transformed, such as described in the example computer program routines illustratively provided in FIG. 5. The transformation may include, for example, determining velocity and/or doubling-time for each of the variables obtained. Thus, some embodiments of block 260 may be carried out using the example computer program routines illustratively provided in FIG. 5, which may be implemented using the R-system packages, as described in relation to FIG. 1A.

At block 270, a predicted probability of agent efficacy in retarding CKD progression is calculated. Some embodiments of block 270 may be carried out using the example computer program routines illustratively provided in FIG. 5, which may be implemented using the R system packages described in relation to FIG. 1A. Some embodiments of block 270 may use a logistic regression model for determining the prediction. Other embodiments of block 270 may use a neural network, support vector machine model, and/or other classifier model. In some embodiments, the probability determined in step 270 is a score corresponding to a likelihood of CKD progression.

At block 280, one or more clinicians or caregivers may be notified of the efficacy of the treatment for a particular patient. In some embodiments of block 280, a threshold is applied to the probability/score determined in block 270, and if the threshold is satisfied, then clinicians and/or caregivers are notified and/or instructed for a particular intervention or other action (e.g., preparing a treatment plan, executing a patient visit, preparing additional medication or therapeutic treatment, etc.). The threshold may be set by a clinician, health care provider, and/or may be determined empirically. At block 285, it is determined whether to continue receiving additional measurements of urine osmolality and/or serum sodium concentration and corresponding date-time stamps. If so, then method 200 proceeds to block 210, as described above, and if no, then the method 200 ends.

Figure 4:
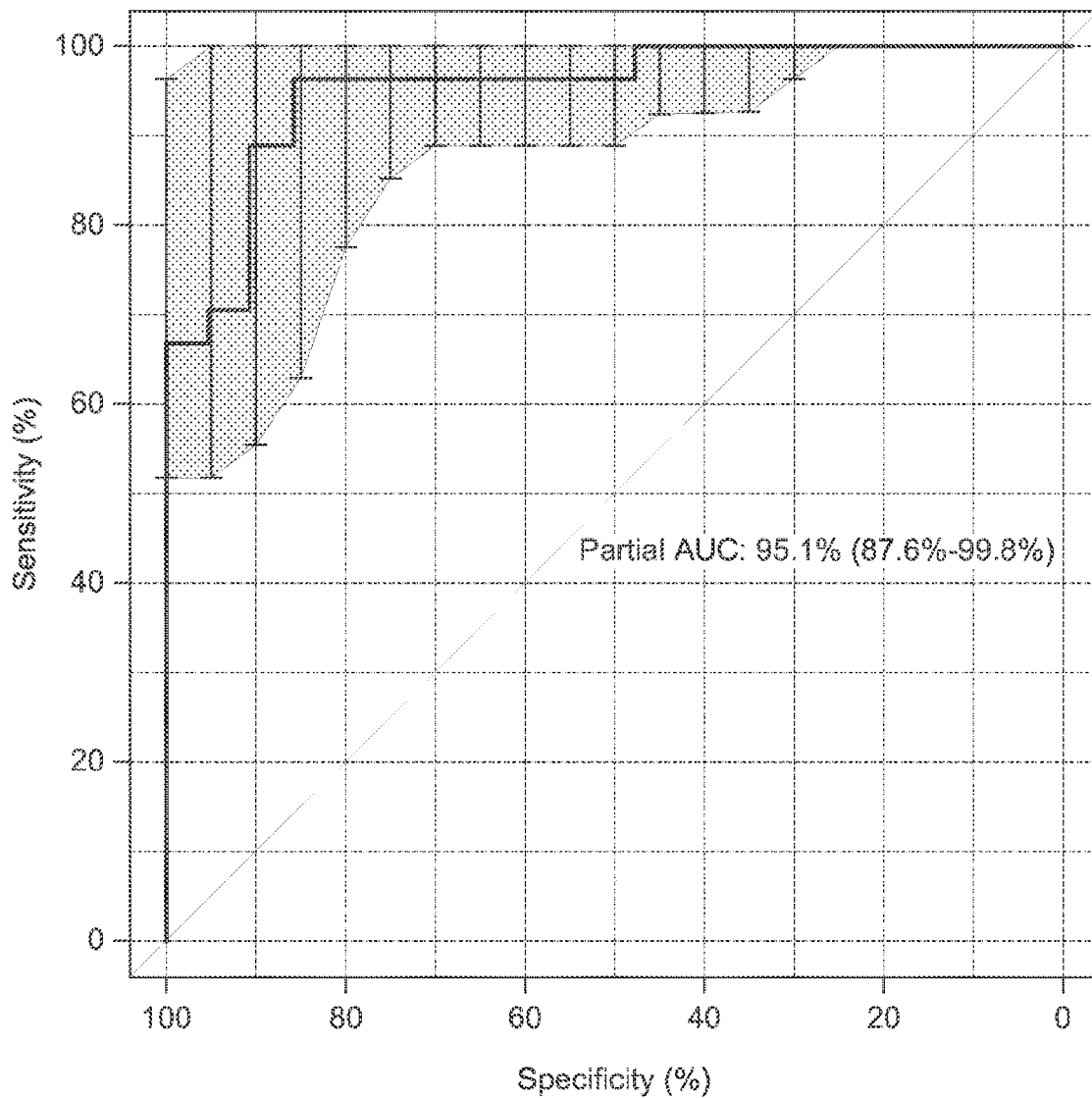
FIG. 4 depicts a Receiver Operating Characteristic (ROC) curve representing the accuracy and discriminating classificatory capacity of the present technology in a cohort of 49 subjects, in accordance with an embodiment of the present disclosure.

With reference to FIGS. 3-5, an exemplary embodiment of the technology reduced to practice for a time series multi-variable properties-based prediction and prevention of CKD progression is provided, in accordance with an embodiment of the present disclosure. In this example, records have been retrieved from a patient health records data warehouse, which is derived from Cerner electronic health records (EHR) from 100% of episodes of care that are incident upon the participating health institutions. The personally identifiable information was removed in conformance with U.S. HIPAA laws and regulations, and the de-identified data has been stored in a separate, secure database. A total of 40,181 ambulatory patient records, which contained four or more date-time stamped values for each of a variety of laboratory and physiologic parameters that were contemporaneous with the nephrology clinic episodes are provided.

Two vasopressin antagonists ('vaptans') are now marketed for the treatment of euvolemic (Europe) or euvolemic and hypervolemic (United States) hyponatremia. These are conivaptan for intravenous use and tolvaptan for oral use. Although their specificity and effectiveness are well-established, their indications are not. At present, it is not known which symptoms of hyponatremia and which degree of hyponatremia should serve as indications for vaptans. It is emphasized that vaptans are effective only in the presence of ADH derangement ('SIADH'), but not in the syndrome of nephrogenic antidiuresis. Vaptans decrease the high mortality and morbidity associated with hyponatremia. This is the rationale that presently justifies the cost of chronic vaptan therapy in heart failure CKD. The optimal vaptan regimen (e.g., timing of initiation, dose, dose-escalation/titration, etc.) in Stages 3-4 CKD is currently not established by controlled clinical trials. However, large observational EHR-derived de-identified datasets such as Cerner Health Facts® data warehouse enable (a) to discover context-specific regimens that are safe and effective in delaying progression to Stage 5 CKD (ESRD), requiring dialysis or transplantation, and (b) to develop predictive mathematical models that identify who will benefit from these regimens and who will not, irrespective of whether hyponatremia is present or, if it is present, whether it is severe or symptomatic.

Hyponatremia is 35% prevalent in Stage 3 CKD and 56% prevalent in Stage 4 CKD. A multi-variable predictive model and vaptan regimen offers the opportunity to deliver enhanced clinical outcomes in terms of improved quality of life (QoL), reduced mortality and morbidity, and slowing of CKD progression. For Fresenius, it represents market growth in earlier stage CKD populations. Although the precise mechanism of resistance to AVP antagonists is unknown, observational data confirm that concentrating and diluting ability in the collecting ducts is necessary, but not sufficient, for the efficacy of AVP antagonists, and it is often impaired in the elderly or those with CKD that has already advanced to Stage 5.

Among the prevalent Stage 3 and Stage 4 CKD patients in the Health Facts® cohort, a total of 49 subjects were treated off-label with tolvaptan. Among these, 28 (57.1%) of the 49 patients were responsive to the AVP V2 antagonist. In tolvaptan-exposed patients, the duration of tolvaptan treatment ranged from 240 days to 1,256 days. Although the cohort available was small, Cox proportional hazards regression suggests a substantial retardation of progression to Stage 5 CKD (tolvaptan-exposed vs. controls: 1.9±1.4 years). In tolvaptan-exposed patients, the duration of tolvaptan treatment ranged from 240 days to 1,256 days. Staging of CKD was established as shown in FIG. 3, which is in accordance with K/DOQI and related guidelines.

In some embodiments, a random Forest package implementation of the Random Forest (RF) method was used to identify a subset of parameters whose time-dependent changes in value were associated with future emergence of Stage 5 CKD with a forward time-horizon of 5 years. Two parameters-baseline pre-challenge urine osmolality and percentage decrease in urine osmolality within 4 to 6 hours after administering a 15 mg tolvaptan challenge-were determined to be statistically significant and were retained for subsequent modeling via logistic regression. As shown in FIG. 4, the Receiver Operating Characteristics (ROC) area under the curve in the final model was 0.95.

The as-treated dataset contained measurements of the parameters taken in the course of conventional ordering practices in an ambulatory nephrology clinic setting. Electrolytes, blood urea nitrogen, and creatinine were routinely measured on each clinic visit. However, certain urine chemistry measurements, such as urine sodium and urine osmolality, were measured infrequently and only in a subset of the CKD cohort. As such, it was uncommon to have more than a few measurements of some of the parameters during the 5-year period. Such a low frequency of measurement is not a major impediment to the successful accomplishment of the predictive aim of the present technology. However, in some embodiments, it may be desirable to acquire more frequent measurements, such as quarterly or at other suitable intervals, particularly in populations whose CKD etiology is such as to have elevated risk of accelerated progression to Stage 5 CKD, such as those with polycystic kidney disease (PKD) or IgA nephropathy (Berger's Disease).

Further findings in this convenience cohort included the discovery that some of the patients analyzed were prescribed off-label concomitant TNF-alpha inhibitor treatment for at least a portion of the time when tolvaptan was prescribed. The TNF-alpha inhibitor treatment was deemed to be 'off-label' insofar as there was no other known clinical indication present, such as rheumatoid arthritis, inflammatory bowel disease, psoriasis, or other autoimmune disease. In this sub-cohort, CKD progression was slower than in patients exposed only to tolvaptan. The numbers of such subjects were too small to reach statistical significance. However, this unexpected finding suggests the appealing possibility that a therapeutic challenge with AVP V2 antagonist might indirectly be predictive of responsiveness to multidrug regimens or to monotherapy with agents that are not AVP V2 antagonists, and whose mechanisms of action are unrelated to AVP V2 antagonism or hyponatremia.

These temporal patterns are of such complexity and variability that it would be beyond the capability of a human being to examine the values of the laboratory results for urine osmolality tests and determine a prediction for progression to Stage 5 CKD that has not yet materialized. Through some embodiments of this disclosure, it is shown that temporal changes in urine osmolality values—either jointly or separately—can serve as a reliable composite leading indicator of (a) therapeutic efficacy of an AVP V2 antagonist in retarding CKD progression, and (b) of subsequent progression to Stage 5 CKD. Another aspect of the technology concerns (a) determining at least one temporal property of a post-challenge urine osmolality time series, such as a percentage change from baseline or velocity, (b) the transformation of the at least one temporal property to an integer score, (c) the combining of the evidence via a multi-variable predictive model, such as a logistic regression equation to form a quantitative probability of Stage 5 CKD materializing within a subsequent time interval, and (d) the rendering of the predicted probability to one or more human decision-makers in the context of an electronic health record information system.

Figure 6:
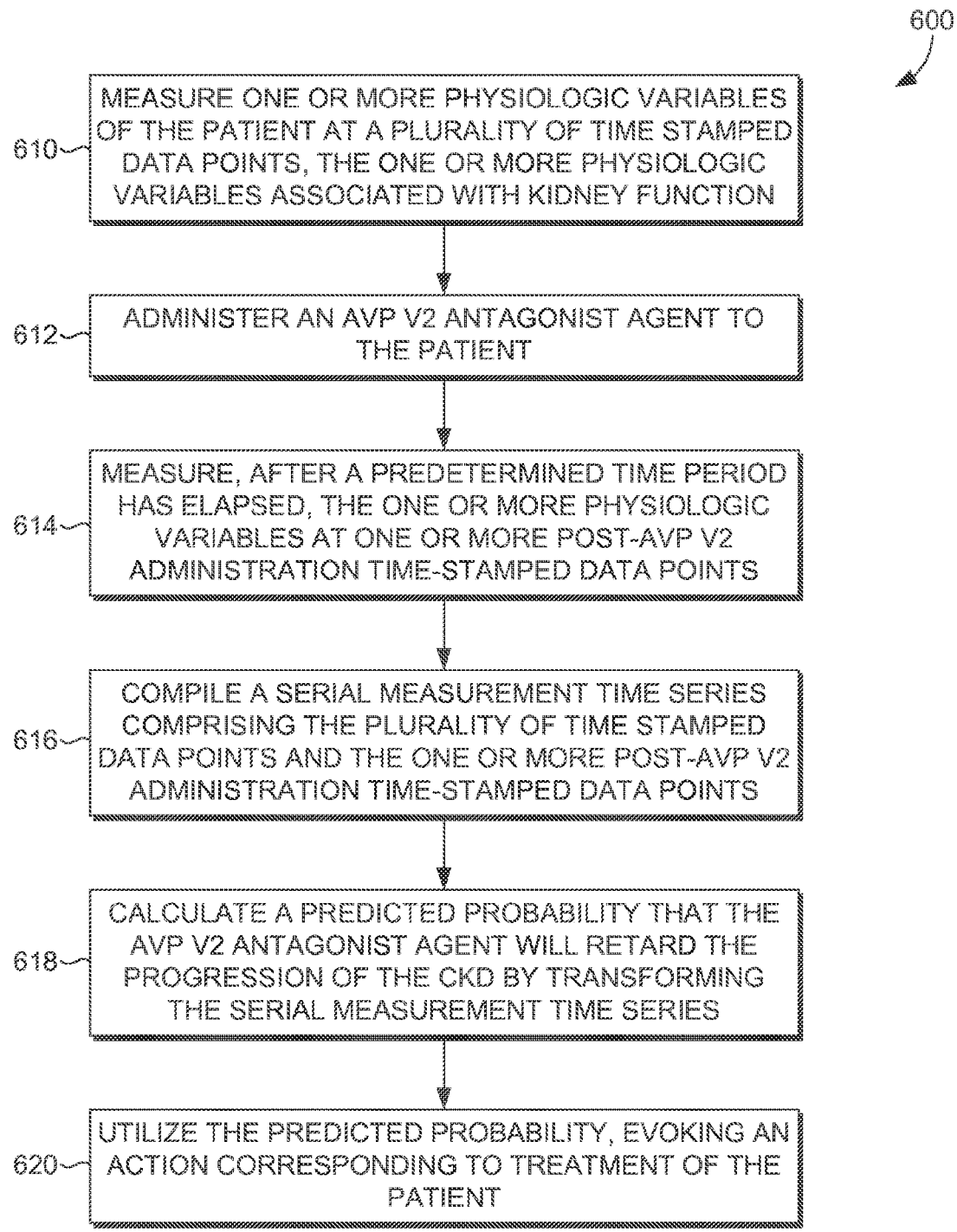
FIGS. 6-7 depict a flow diagram of methods for predicting CKD risk and/or progression in an individual, in accordance with an embodiment of the present disclosure.

Turning now to FIG. 6, a block diagram of a method 600 for predicting the progression of chronic kidney disease (CKD) in a patient is provided, in accordance with an embodiment of the present disclosure. At a block 610, one or more physiologic variables of the patient are measured at a plurality of time stamped data points, the one or more physiologic variables associated with kidney function (e.g., urine osmolality or serum sodium). At a block 612, an AVP V2 antagonist agent (e.g., tolvaptan, conivaptan, etc.) is administered to the patient. At a block 614, the one or more physiologic variables are measured, after a predetermined time period has elapsed (e.g., 4-6 hours), at one or more post-AVP V2 administration time stamped data points. At a block 616, a serial measurement time series is compiled comprising the plurality of time stamped data points and the one or more post-AVP V2 administration time stamped data points. At a block 618, a predicted probability that the AVP V2 antagonist agent will retard the progression of the CKD is calculated by transforming the serial measurement time series (e.g., using a logistic regression model, neural network, or support vector machine model). At a block 620, utilizing the predicted probability, an action is evoked corresponding to treatment of the patient (e.g., providing a notification to a clinician, automatically generating a treatment plan for the patient, scheduling resources or personnel for treatment, entering information into a patient record, such as an EHR, etc.).

Figure 7:
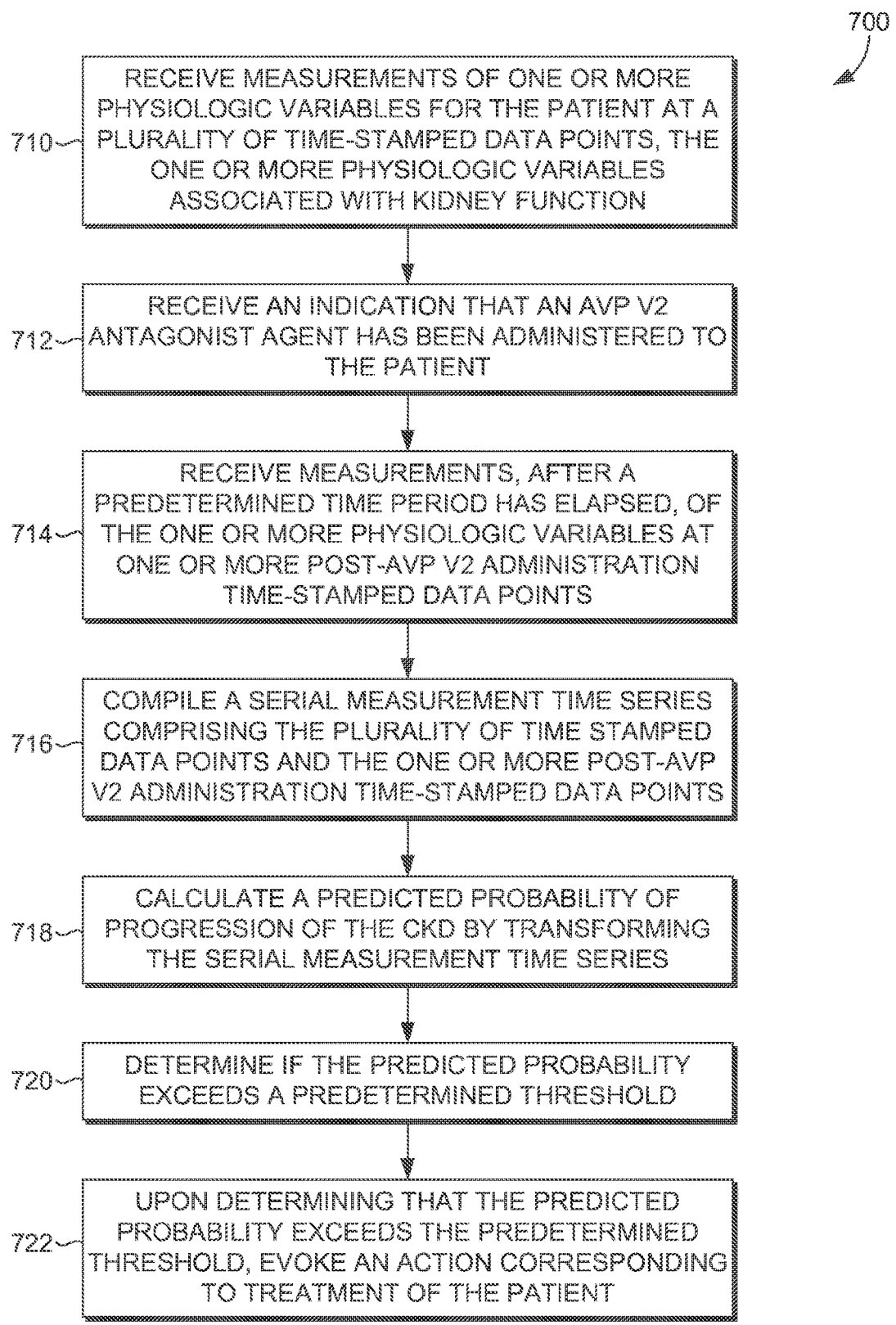

Turning now to FIG. 7, a block diagram of an exemplary method 700 for predicting the progression of chronic kidney disease (CKD) in a patient is provided, in accordance with an embodiment of the present disclosure. At a block 710, measurements of one or more physiologic variables for the patient at a plurality of time stamped data points are received, the one or more physiologic variables associated with kidney function. At a block 712, an indication that an AVP V2 antagonist agent has been administered to the patient is received. At a block 714, after a predetermined time period has elapsed, measurements of the one or more physiologic variables at one or more post-AVP V2 administration time stamped data points are received. At a block 716, a serial measurement time series comprising the plurality of time stamped data points and the one or more post-AVP V2 administration time stamped data points is compiled. At a block 718, a predicted probability of progression of the CKD is calculated by transforming the serial measurement time series. At a block 720, it is determined if the predicted probability exceeds a predetermined threshold. At a block 722, upon determining that the predicted probability exceeds the predetermined threshold, an action corresponding to treatment of the patient is evoked.

Embodiment 1: A method for predicting the progression of Chronic Kidney Disease (CKD) in a patient. The method comprises measuring one or more physiologic variables of the patient at a plurality of time stamped data points, the one or more physiologic variables associated with kidney function; administering an AVP V2 antagonist agent to the patient; measuring, after a predetermined time period has elapsed, the one or more physiologic variables at one or more post-AVP V2 administration time stamped data points; compiling a serial measurement time series comprising the plurality of time stamped data points and the one or more post-AVP V2 administration time stamped data points; calculating a predicted probability that the AVP V2 antagonist agent will retard the progression of the CKD by transforming the serial measurement time series; and utilizing the predicted probability, evoking an action corresponding to treatment of the patient.

Embodiment 2: The method of embodiment 1, further comprising censoring any of the plurality of time stamped data points affected by at least one of error and measurement artifact.

Embodiment 3: The method of any of embodiments 1-2, wherein transforming the serial measurement time series comprises using at least one of the following on the serial measurement time series: a logistic regression model, a neural network, and a support vector machine model.

Embodiment 4: The method of any of embodiments 1-3, further comprising transforming the plurality of time stamped data points by performing at least one of determining a velocity of the serial measurement time series and determining a doubling-time for each of the measured one or more physiologic variables in the serial measurement time series.

Embodiment 5: The method of any of embodiments 1-4, wherein the one or more physiologic variables comprise at least one of urine osmolality of the patient and serum sodium of the patient.

Embodiment 6: The method of any of embodiments 1-5, wherein the plurality of time stamped data points comprises two time stamp data points.

Embodiment 7: The method of any of embodiments 1-6, wherein the predetermined time period is between 4 and 6 hours inclusive.

Embodiment 8: The method of any of embodiments 1-7, wherein the measured one or more physiologic variables from the plurality of time stamped data points are received from an Electronic Health Record (EHR).

Embodiment 9: The method of any of embodiments 1-8, wherein the AVP V2 antagonist agent comprises at least one of tolvaptan, conivaptan, and serum sodium concentration.

Embodiment 10: One or more computer-readable media having computer-executable instructions embodied thereon that, when executed, facilitate a method for predicting the progression of chronic kidney disease (CKD) in a patient. The method comprises receiving measurements of one or more physiologic variables for the patient at a plurality of time stamped data points, the one or more physiologic variables associated with kidney function; receiving an indication that an AVP V2 antagonist agent has been administered to the patient; receiving measurements, after a predetermined time period has elapsed, of the one or more physiologic variables at one or more post-AVP V2 administration time stamped data points; compiling a serial measurement time series comprising the plurality of time stamped data points and the one or more post-AVP V2 administration time stamped data points; calculating a predicted probability of progression of the CKD by transforming the serial measurement time series; determining if the predicted probability exceeds a predetermined threshold; and upon determining that the predicted probability exceeds the predetermined threshold, evoking an action corresponding to treatment of the patient.

Embodiment 11: The computer-readable media of embodiment 10, wherein the action corresponding to treatment of the patient comprises at least one of initiating a signal that causes an alert to be presented to a clinician, initiating a signal for a plan of care to be initiated for the patient, preparing a treatment plan for the patient, automatically scheduling a caregiver to provide therapeutic treatment to the patient, and modifying or generating a healthcare computer program for treating the patient.

Embodiment 12: The computer-readable media of any of embodiments 10-11, wherein transforming the serial measurement time series comprises using at least one of the following on the serial measurement time series: a logistic regression model, a neural network, and a support vector machine model.

Embodiment 13: The computer-readable media of any of embodiments 10-12, wherein the one or more physiologic variables comprises at least one of urine osmolality of the patient and serum sodium of the patient.

Embodiment 14: The computer-readable media of any of embodiments 10-13, wherein the method further comprises censoring any value or range of the serial measurement time series affected by error or measurement artifact.

Embodiment 15: The computer-readable media of any of embodiments 10-14, wherein the predetermined time period comprises between 4 and 6 hours inclusive.

Embodiment 16: The computer-readable media of any of embodiments 10-15, wherein the one or more physiologic variables from the plurality of time stamped data points are received from an Electronic Health Record (EHR).

Embodiment 17: The computer-readable media of any of embodiments 10-16, wherein the AVP V2 antagonist agent comprises at least one of tolvaptan, conivaptan, and serum sodium concentration.

Embodiment 18: A system for predicting the progression of chronic kidney disease (CKD) in a patient. The system comprises one or more processors, one or more sensors configured to measure one or more physiologic variables for the patient, the one or more physiologic variables associated with kidney function; and computer storage memory having computer-executable instructions stored thereon that, when executed by the processor, implement a method comprising receiving measurements of the one or more physiologic variables for the patient at a plurality of time stamped data points; receiving an indication that an AVP V2 antagonist agent has been administered to the patient; receiving measurements, after a predetermined time period has elapsed, of the one or more physiologic variables at one or more post-AVP V2 administration time stamped data points; compiling a serial measurement time series comprising the plurality of time stamped data points and the one or more post-AVP V2 administration time stamped data points; calculating a predicted probability of progression of the CKD of the patient by transforming the serial measurement time series; determining if the predicted probability exceeds a predetermined threshold; and upon determining that the predicted probability exceeds the predetermined threshold, evoking an action corresponding to treatment of the patient.

Embodiment 19: The system of embodiment 18, wherein the action corresponding to treatment of the patient comprises at least one of initiating a signal that causes an alert to be presented to a clinician, initiating a signal for a plan of care to be initiated for the patient, automatically scheduling a caregiver to provide therapeutic treatment to the patient, and modifying or generating a healthcare computer program for treating the patient.

Embodiment 20: The system of any of embodiments 18-19, wherein transforming the serial measurement time series comprises using at least one of the following on the serial measurement time series: a logistic regression model, a neural network, and a support vector machine model.

Many different arrangements of the various components depicted, as well as use of components not shown, are possible without departing from the spirit and scope of the present disclosure. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and sub-combinations are of utility and may be employed without reference to other features and sub-combinations and are contemplated within the scope of the claims. Not all steps listed in the various figures need be carried out in the specific order described. Accordingly, the scope of the invention is intended to be limited only by the following claims.

What is claimed is:

1. A method for predicting a progression of Chronic Kidney Disease (CKD) in a patient, the method comprising:
   measuring one or more physiologic variables of the patient at a plurality of time stamped data points;
   administering one or more agents to the patient;
   measuring, after a predetermined time period has elapsed, the one or more physiologic variables at one or more post-agent administration of one or more agents time stamped data points;
   compiling a serial measurement time series comprising the plurality of time stamped data points and the one or more post-agent administration time stamped data points;
   calculating a predicted probability that the one or more agents will retard a progression of an illness;
   utilizing the predicted probability, evoking an action corresponding to treatment of the patient.

2. The method of claim 1, further comprising censoring any of the plurality of time stamped data points affected by at least one of:
   error; and
   measurement artifact.

3. The method of claim 1, further comprising transforming the plurality of time stamped data points by performing at least one of:
   determining a velocity of the serial measurement time series; and
   determining a doubling-time for each of the measured one or more physiologic variables in the serial measurement time series.

4. The method of claim 1, wherein the one or more agents comprises an Arginine Vasopressin (AVP) V2 antagonist agent.

5. The method of claim 1, wherein the one or more physiologic variables comprise at least one of:
   urine osmolality of the patient; and
   serum sodium of the patient.

6. The method of claim 1, wherein the plurality of time stamped data points comprises two time stamp data points.

7. The method of claim 1, wherein the predetermined time period is between 4 and 6 hours inclusive.

8. The method of claim 1, wherein the measured one or more physiologic variables from the plurality of time stamped data points are received from an Electronic Health Record (EHR).

9. The method of claim 4, wherein the AVP V2 antagonist agent comprises at least one of:
   tolvaptan;
   conivaptan; and
   serum sodium concentration.

10. One or more non-transitory computer-readable media having computer-executable instructions embodied thereon that, when executed, facilitate a method for predicting a progression of Chronic Kidney Disease (CKD) in a patient the method comprising:
    measuring one or more physiologic variables of the patient at a plurality of time stamped data points;
    administering one or more agents to the patient;
    measuring, after a predetermined time period has elapsed, the one or more physiologic variables at one or more post-administration of one or more agents time stamped data points;
    compiling a serial measurement time series comprising the plurality of time stamped data points and the one or more post-agent administration time stamped data points;
    calculating a predicted probability that the one or more agents will retard a progression of an illness;
    utilizing the predicted probability, evoking an action corresponding to treatment of the patient.

11. The non-transitory computer-readable media of claim 10, wherein the action corresponding to the treatment of the patient comprises at least one of:
    initiating a signal that causes an alert to be presented to a clinician;
    initiating a signal for a plan of care to be initiated for the patient;
    preparing a treatment plan for the patient;
    automatically scheduling a caregiver to provide therapeutic treatment to the patient; and
    modifying or generating a healthcare computer program for treating the patient.

12. The non-transitory computer-readable media of claim 10, wherein the one or more agents comprises an Arginine Vasopressin (AVP) V2 antagonist agent.

13. The non-transitory computer-readable media of claim 10, wherein the one or more physiologic variables comprises at least one of:

urine osmolality of the patient; and serum sodium of the patient.

14. The non-transitory computer-readable media of claim 10, wherein the method further comprises censoring any value or range of the serial measurement time series affected by error or measurement artifact.

15. The non-transitory computer-readable media of claim 10, wherein the predetermined time period comprises between 4 and 6 hours inclusive.

16. The non-transitory computer-readable media of claim 10, wherein the one or more physiologic variables from the plurality of time stamped data points are received from an Electronic Health Record (EHR).

17. The non-transitory computer-readable media of claim 12, wherein the AVP V2 antagonist agent comprises at least one of:

tolvaptan;

conivaptan; and serum sodium concentration.

18. A system for predicting a progression of Chronic Kidney Disease (CKD) in a patient, the system comprising:

one or more processors;

one or more sensors configured to measure one or more physiologic variables for the patient, the one or more physiologic variables associated with kidney function; and computer storage memory having computer-executable instructions stored thereon that, when executed by the one or more processors, implement a method comprising:

administering one or more agents to the patient;

measuring, after a predetermined time period has elapsed, the one or more physiologic variables at one or more post-administration of one or more agents time stamped data points;

compiling a serial measurement time series comprising the time stamped data points and the one or more post-agent administration time stamped data points;

calculating a predicted probability that the one or more agents will retard the progression of an illness;

utilizing the predicted probability, evoking an action corresponding to treatment of the patient.

19. The system of claim 18, wherein the action corresponding to treatment of the patient comprises at least one of:

initiating a signal that causes an alert to be presented to a clinician;

initiating a signal for a plan of care to be initiated for the patient;

automatically scheduling a caregiver to provide therapeutic treatment to the patient; and modifying or generating a healthcare computer program for treating the patient.

20. The system of claim 18, wherein transforming the serial measurement time series comprises using at least one of the following on the serial measurement time series:

a logistic regression model;

a neural network; and a support vector machine model.

* * * * *